(12) United States Patent
Liu et al.

(10) Patent No.: US 11,031,108 B2
(45) Date of Patent: Jun. 8, 2021

(54) MEDICINE MANAGEMENT METHOD AND MEDICINE MANAGEMENT DEVICE

(71) Applicant: HTC Corporation, Taoyuan (TW)

(72) Inventors: Tsung-Hsiang Liu, Taoyuan (TW);
Ya-Han Yang, Taoyuan (TW);
Hao-Ting Chang, Taoyuan (TW);
Chih-Wei Cheng, Taoyuan (TW);
Ting-Jung Chang, Taoyuan (TW)

(73) Assignee: HTC Corporation, Taoyuan (TW)

( * ) Notice: Subject to any disclaimer, the term of this patent is extended or adjusted under 35 U.S.C. 154(b) by 248 days.

(21) Appl. No.: 15/427,036

(22) Filed: Feb. 7, 2017

(65) Prior Publication Data

US 2017/0286634 A1 Oct. 5, 2017

(30) Foreign Application Priority Data

Mar. 31, 2016 (TW) .................................. 105110680

(51) Int. Cl.
*G16H 10/60* (2018.01)
*G16H 20/10* (2018.01)
*G06Q 10/10* (2012.01)

(52) U.S. Cl.
CPC ............. *G16H 10/60* (2018.01); *G16H 20/10* (2018.01); *G06Q 10/109* (2013.01)

(58) Field of Classification Search
CPC ... G06F 19/3456; G16H 10/60; G06Q 10/109
USPC ........................................................ 705/2–4
See application file for complete search history.

(56) References Cited

U.S. PATENT DOCUMENTS

| 2005/0010409 | A1* | 1/2005 | Hull ....................... G06K 15/00 704/243 |
| 2007/0260479 | A1* | 11/2007 | Duckert .............. G06F 19/3456 705/2 |
| 2009/0105560 | A1* | 4/2009 | Solomon .............. A61B 5/0002 600/301 |
| 2014/0337052 | A1* | 11/2014 | Pellini .................... G16H 15/00 705/3 |

(Continued)

FOREIGN PATENT DOCUMENTS

| CN | 102542176 A | 7/2012 |
| CN | 202784113 U | 3/2013 |

(Continued)

OTHER PUBLICATIONS

Stange, Dorit, et al. "Medication complexity, prescription behaviour and patient adherence at the interface between ambulatory and stationary medical care." European journal of clinical pharmacology 69.3 (2013): 573-580. (Year: 2013).*

(Continued)

*Primary Examiner* — Mark Holcomb
(74) *Attorney, Agent, or Firm* — CRC & Partners Co., LLC (57) ABSTRACT

A medicine management method includes acquiring user information of medicine usage corresponding to at least one assigned medicine; acquiring user information of medicine using reactions; and displaying the user information of medicine usage with first time information corresponding to different time points of using the at least one assigned medicine and the user information of medicine using reactions with second time information corresponding to different time points of occurring medicine using reactions concurrently.

20 Claims, 6 Drawing Sheets

(56) References Cited

U.S. PATENT DOCUMENTS

| | | | |
|---|---|---|---|
| 2016/0026773 A1* | 1/2016 | Chu | A61J 7/02 |
| | | | 705/2 |
| 2016/0371459 A1* | 12/2016 | Minemura | G06Q 50/24 |
| 2017/0262604 A1* | 9/2017 | Francois | G06F 19/3418 |

FOREIGN PATENT DOCUMENTS

| | | |
|---|---|---|
| CN | 104000726 A | 8/2014 |
| CN | 104537265 A | 4/2015 |
| CN | 204614037 U | 9/2015 |
| TW | 201010666 A | 3/2010 |
| TW | 201117803 A | 6/2011 |
| WO | 2007130781 A2 | 11/2007 |

OTHER PUBLICATIONS

Corresponding Taiwan office action dated Dec. 25, 2018.
Corresponding Chinese office action dated Mar. 2, 2020.

* cited by examiner

MEDICINE MANAGEMENT METHOD AND MEDICINE MANAGEMENT DEVICE

This application claims priority to Taiwan Application Serial Number 105110680, filed Mar. 31, 2016, which is herein incorporated by reference.

BACKGROUND

Technical Field

The present disclosure relates to an electronic device and a method. More particularly, the present disclosure relates to a medicine management device and a medicine management method.

Description of Related Art

With advances in electronic technology, medicine management devices are being increasingly used.

After obtaining medicine, a patient has to use the medicine regularly, and moreover, must report on any reaction to the medicine on his or her body to the doctor to facilitate subsequent medical treatment. However, there are many reasons why a doctor is unable to track the effects of the medicine, such as the patient forgetting to use the medicine or the patient forgetting the physical reaction to the medicine. Thus, a method to solve such a problem is desired.

SUMMARY

One aspect of the present disclosure is related to a medicine management method. In accordance with one embodiment of the present disclosure, the medicine management method includes acquiring user information of medicine usage corresponding to at least one assigned medicine, wherein the user information of medicine usage comprises first time information corresponding to different time points of using the at least one assigned medicine; acquiring user information of medicine using reactions, wherein the user information of medicine using reactions comprises second time information corresponding to different time points of occurring medicine using reactions; and displaying the user information of medicine usage with the first time information and the user information of medicine using reactions with the second time information concurrently.

Another aspect of the present disclosure is related to a medicine management device. In accordance with one embodiment of the present disclosure, the medicine management device includes a display and a processor. The processor is electrically connected to the display. The processor is configured for acquiring user information of medicine usage corresponding to at least one assigned medicine, wherein the user information of medicine usage comprises first time information corresponding to different time points of using the at least one assigned medicine; acquiring user information of medicine using reactions, wherein the user information of medicine using reactions comprises second time information corresponding to different time points of occurring medicine using reactions; and controlling the display to display the user information of medicine usage with the first time information and the user information of medicine using reactions with the second time information concurrently.

Another aspect of the present disclosure is related to a medicine management method. In accordance with one embodiment of the present disclosure, the medicine management method includes acquiring a time of using at least one assigned medicine; acquiring at least one physical/personal parameter; determining a reaction request time for displaying a reaction request operation according to the time of using at least one assigned medicine and the at least one physical/personal parameter; and executing the reaction request operation to acquire user information of reactions.

Through the operations of one embodiment described above, a doctor can concurrently view patient information related to medicine usage and patient information related to symptoms after using medicine, both in a way corresponding to different times. This information can be advantageously used by the doctor to proceed with subsequent treatment.

BRIEF DESCRIPTION OF THE DRAWINGS

The invention can be more fully understood by reading the following detailed description of the embodiments, with reference made to the accompanying drawings as follows.

DETAILED DESCRIPTION

Reference will now be made in detail to the present embodiments of the invention, examples of which are illustrated in the accompanying drawings. Wherever possible, the same reference numbers are used in the drawings and the description to refer to the same or like parts.

It will be understood that, in the description herein and throughout the claims that follow, when an element is referred to as being "connected" or "coupled" to another element, it can be directly connected or coupled to the other element or intervening elements may be present. Moreover, "electrically connect" or "connect" can further refer to the interoperation or interaction between two or more elements.

It will be understood that, in the description herein and throughout the claims that follow, although the terms "first," "second," etc. may be used to describe various elements, these elements should not be limited by these terms. These terms are only used to distinguish one element from another.

It will be understood that, in the description herein and throughout the claims that follow, the terms "comprise" or "comprising," "include" or "including," "have" or "having," "contain" or "containing" and the like used herein are to be understood to be open-ended, i.e., to mean including but not limited to.

It will be understood that, in the description herein and throughout the claims that follow, the phrase "and/or" includes any and all combinations of one or more of the associated listed items.

One aspect of the present disclosure is related to a medicine management device. In the paragraphs below, a smart phone or a tablet computer will be taken as an example to describe details of the medicine management device. However, the present disclosure is not limited to the embodiment described below.

Figure 1:
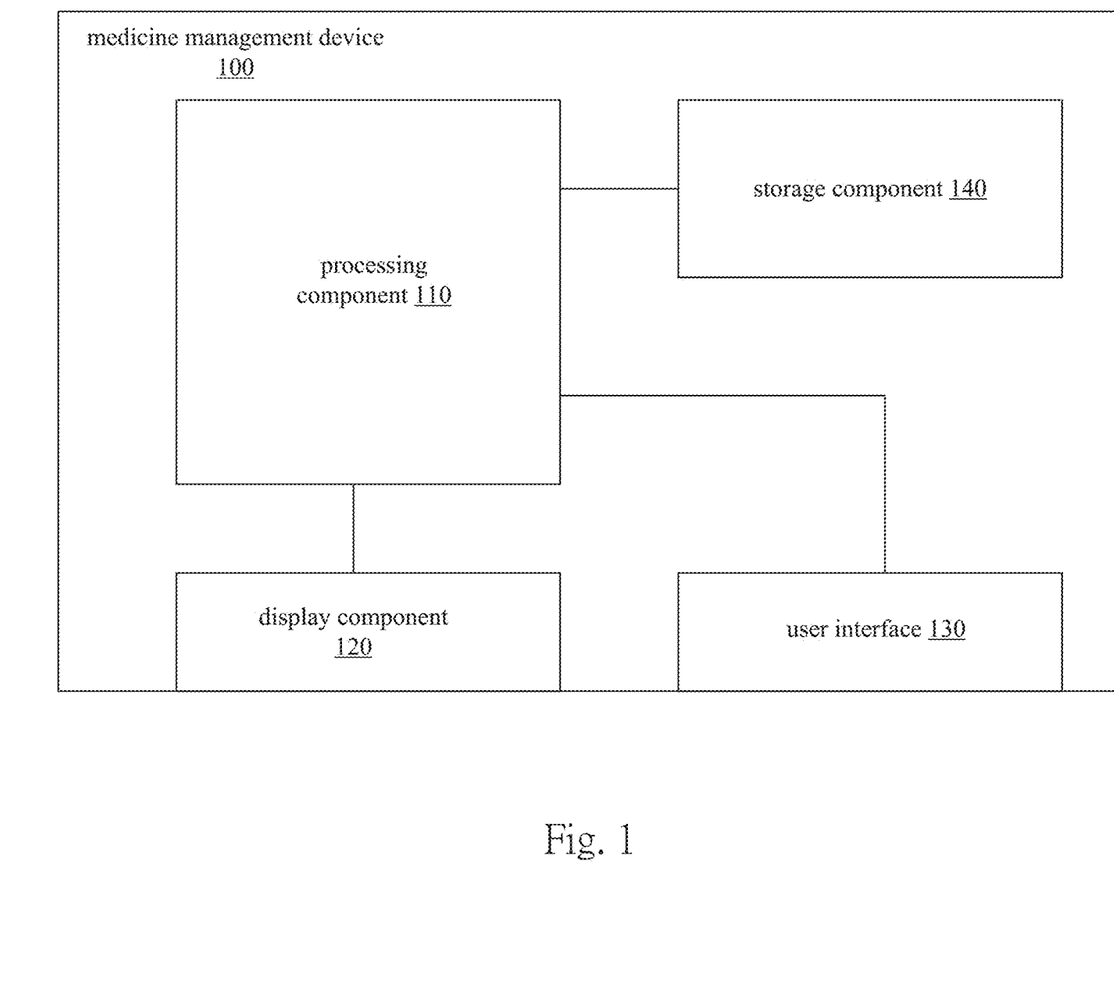
FIG. 1 is a schematic block diagram of a medicine management device in accordance with one embodiment of the present disclosure.

FIG. 1 is a schematic block diagram of a medicine management device 100 in accordance with one embodiment of the present disclosure. In this embodiment, the medicine management device 100 includes a processing component 110, a display component 120, a user input interface 130, and a storage component 140. The processing component 110 is electrically connected to the display component 120, the user input interface 130, and the storage component 140.

In one embodiment, the processing component 110 can be realized by, for example, a processor, such as a central processor or a microprocessor, but is not limited in this regard. The display component 120 can be realized by, for example, a display, such as a liquid crystal display, an active matrix organic light emitting display (AMOLED), or an e-paper display, but is not limited in this regard. The user input interface 130 can be realized by, for example, a touch sensing module, a keyboard, or a mouse, but is not limited in this regard. The storage component 140 may be realized by a read-only memory (ROM), a flash memory, a floppy disk, a hard disk, an optical disc, a flash disk, a flash drive, a tape, a database accessible from a network, or any storage medium with the same functionality that can be contemplated by persons of ordinary skill in the art to which this invention pertains. In one embodiment, the display component 120 and the user input interface 130 can be integrated as a touch display component, but the present disclosure is not limited in this regard.

The medicine management device 100 may store a medicine database through the storage component 140. The medicine database stores information relevant to various kinds of medicines (including suppositories, and medicines for external and internal application), such as information related to the external appearance of medicines, usage information of medicines, reaction information related to medicines (e.g., fever, dizziness, dyspnoea). It should be noted that, in different embodiments, the content of the medicine database can be updated through a cloud device.

A user can input information, so that the medicine management device 100 can acquire a daily schedule of the user. The daily schedule of the user includes times that the user wakes, goes to bed, and has meals. The medicine management device 100 can remind the user when and how to use the medicine according to the daily schedule of the user, and record the status of medicine usage and the corresponding reactions of the body, to facilitate subsequent medical treatment.

The processing component 110 can acquire information relevant to at least one assigned medicine. The information relevant to the at least one assigned medicine includes a medicine instruction (e.g., used after meals or used at bedtime), and a prescribed quantity of the at least one assigned medicine. For example, after the user gets a prescription from a doctor, the processing component 110 can acquire the information relevant to the at least one assigned medicine by scanning a two-dimensional code (e.g., on the prescription) via a camera, or receive a user input via the user input interface 130. The processing component 110 can determine whether the data provided from the scanned two-dimensional code can be identified or conforms to predefined data formats. If not, the processing component 110 can control the display component 120 to display an error message, so as to prompt the user to manually input the information relevant to the at least one assigned medicine via the user input interface 130.

The processing component 110 can determine one or more medicine reminding times according to the medicine instruction of the at least one assigned medicine and the daily schedule. Subsequently, the processing component 110 can execute medicine reminding operations according to the medicine reminding times.

Figure 2:
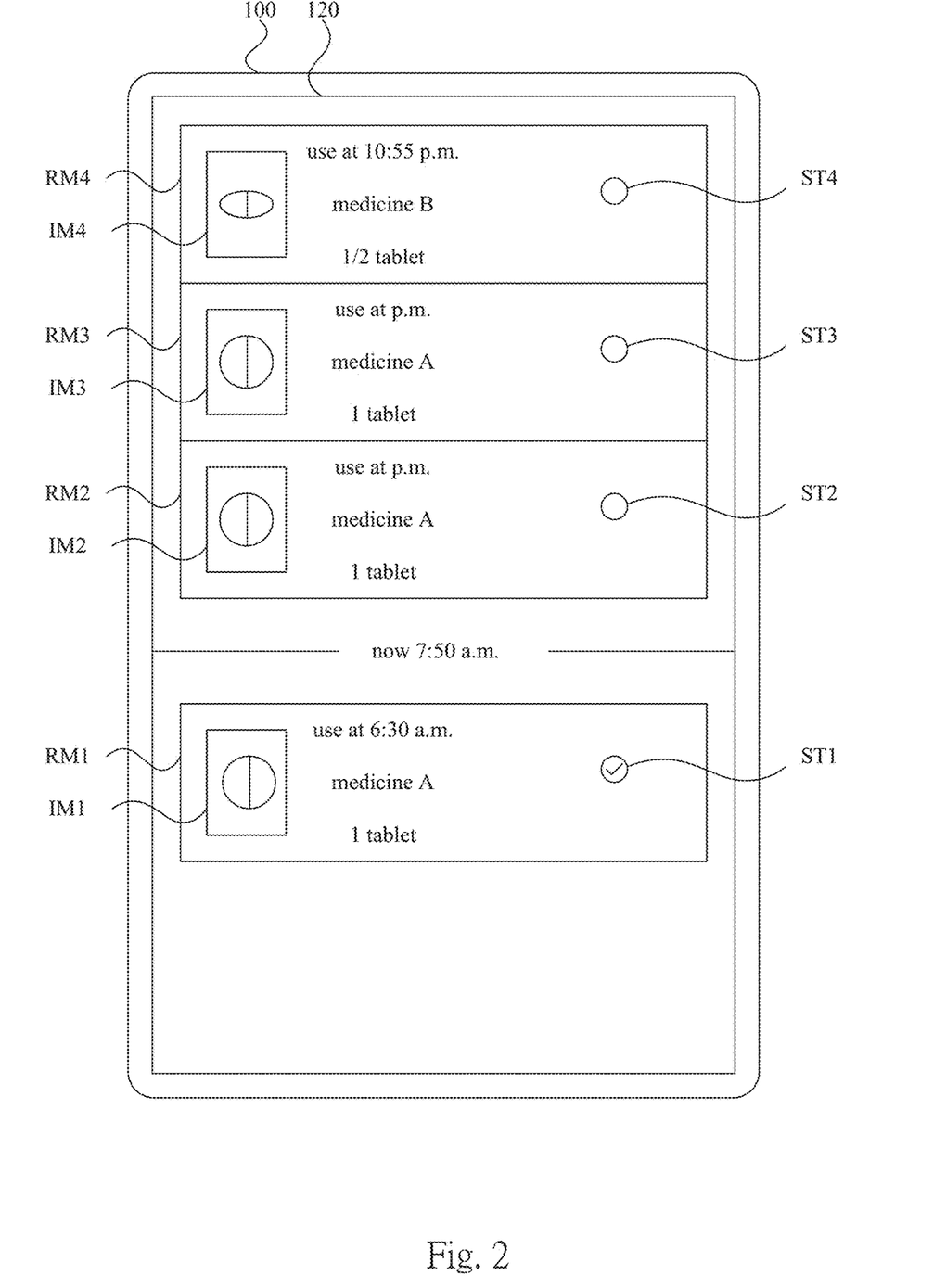
FIG. 2 illustrates an example of an operation diagram of the medicine management device in accordance with one embodiment of the present disclosure.

For example, referring to FIG. 2, in one embodiment, the medicine management device 100 acquires information relevant to a medicine A, in which the medicine A should be used after meals. When the times for meals in the daily schedule of the user is 6:00 AM, 12:00 PM, and 6:00 PM, the processing component 110 can delay the times for meals by a delay time (e.g., 30 minutes) to serve as the medicine reminding times (i.e., 6:30 AM, 12:30 PM, and 6:30 PM).

In addition, the medicine management device 100 acquires information relevant to a medicine B, in which the medicine B should be used at bedtime. When the time for bed in the daily schedule of the user is 11:00 PM, the processing component 110 can move up the time for bed ahead by a predetermined time (e.g., 5 minutes) to serve as the medicine reminding time (i.e., 10:55 PM).

The processing component 110 can execute a medicine reminding operation at the medicine reminding time. For example, the processing component 110 may control the display component 120 to display a reminding message and/or activate an alarm.

In this operative example, the processing component 110 can control the display component 120 to display reminding data RM1-RM3 corresponding to the medicine A and reminding data RM4 corresponding to the medicine B. Each of the reminding data RM1-RM4 includes a medicine reminding time, a medicine name, and a dosage. In addition, in this operative example, the reminding data RM1-RM4 further includes status indications ST1-ST4 indicating whether the user has used the medicine. For example, when the user has used the medicine corresponding to the reminding data RM1, the status indication ST1 displays a first icon (e.g., a circle with a check mark or a solid circle). When the user has not used the medicine corresponding to the reminding data RM1, the status indication ST1 displays a second icon (e.g., a circle with an exclamation mark). The status indications (e.g., ST2-ST4) corresponding to the reminding data with the times in the future (e.g., the reminding data RM2-RM4) display third icons (e.g., display hollow circles).

In this operative example, after each time the user use the medicine corresponding to the reminding data RM1-RM4, the user can input usage information (e.g., including the actual time of using the medicine and/or the actual dose of the medicine), so that the processing component 110 can accordingly update user information of medicine usage corresponding to the medicine A and medicine B (e.g., including whether the user uses the medicine, the actual time of the user using the medicine, and/or the actual dose of the medicine the user has used). In one embodiment, the user information of medicine usage includes first time information corresponding to different time points of using the medicine A and medicine B. Each time the user information of medicine usage corresponding to the medicine A and the medicine B is updated, the corresponding status indications ST1-ST4 are also changed. For example, after the user updates the user information of medicine usage corresponding to the reminding data RM1 (changed from not yet used to used), the status indication ST1 will be changed accordingly.

In this operative example, the reminding data RM1-RM4 further include photographs IM1-IM4 of the corresponding medicines, so as to help prevent the user from using the wrong medicine. For example, the photographs IM1-IM3 corresponding to the medicine A is presented on the reminding data RM1-RM3, and the photograph IM4 corresponding to the medicine B is presented on the reminding data RM4.

In one embodiment, the user can also manually input commands to change the medicine reminding times in the reminding data RM1-RM4, so as to make the medicine reminding times more appropriate. In one embodiment, the user can manually input a command to add a new reminding data (e.g., add a reminding data corresponding to the medicine A, in which the medicine reminding time is 10:55 PM).

In one embodiment, the user can also manually input a command to selectively omit a certain reminding data. The processing component 110 can record the omission corresponding to the user command and update the user information of medicine usage. In one embodiment, the medicine management device 100 is designed to allow the user to omit reminding data, but prohibit the user from deleting any reminding data, so that the medicine usage status can be exactly recorded.

In one embodiment, the processing component 110 can acquire a prescribed quantity of the assigned medicine according to the two-dimensional code described above or by manual input. The processing component 110 can calculate a time for going back to a doctor according to the medicine instructions of the assigned medicine and the prescribed quantity of the assigned medicine. For example, under a condition that the prescribed quantity of the assigned medicine is 21 tablets and the medicine should be used after meals, the time for going back to a doctor can be 7 days later, but is not limited in this regard.

In one embodiment, the processing component 110 can acquire hospital department information of a prescription corresponding to an assigned medicine, medicine information corresponding to an assigned medicine, and doctor information of a prescription corresponding to an assigned medicine according to the two-dimensional code described above. The processing component 110 can also acquire such information from user inputs via the user input interface 130. Subsequently, the processing component 110 can adjust the time for going back to a doctor according to at least one of the hospital department information of a prescription corresponding to an assigned medicine, medicine information corresponding to an assigned medicine, and doctor information of a prescription corresponding to an assigned medicine. For example, under a condition that the original calculated time for going back to a doctor is 7 days, if the doctor prescribing the assigned medicine is doctor C, the time for going back to a doctor can be adjusted to 10 days; while if the doctor prescribing the assigned medicine is doctor D, the time for going back to a doctor can be maintained at 7 days.

In one embodiment, the processing component 110 can load the medicine database in the storage component 140 or a cloud device, to acquire possible reaction information of an assigned medicine (e.g., side effects like fever, dizziness, or dyspnoea) after the user has used the assigned medicine. The processing component 110 can control the display component 120 to display a reaction request message, in which the reaction request message corresponds to the possible reaction information of the assigned medicine. For example, if the possible reactions after a medicine Z being used are dyspnoea and nausea, a reaction list including dyspnoea and nausea is presented on the reaction request message, so that the user can check the actual reactions. In addition, an adding function can also be provided, so that the user can add another reaction to the reaction list.

After the reaction request message is displayed, the processing component 110 acquires a user input corresponding to the reaction request message via the user input interface 130, and acquires user information of medicine using reactions (e.g., fever, dizziness, and dyspnoea). In one embodiment, the user information of medicine using reactions includes second time information corresponding to different time points of occurring medicine using reactions (e.g., fever, dizziness, and dyspnoea).

In addition, in one embodiment, the processing component 110 can determine a reaction request time, and control the display component 120 to display the reaction request message according to the reaction request time. In one embodiment, the processing component 110 can determine the reaction request time for displaying the reaction request message according to the first time information, the second information, and at least one physical/personal parameter. In one embodiment, the reaction request message is displayed for acquiring a user input at the reaction request time. In one embodiment, the processing component 110 may acquire statistical information of reaction occurring time (e.g., the side effects that statistically occur after 1 hour of using the medicine) corresponding to the assigned medicine from the medicine database in the storage component 140 or a cloud device, and the processing component 110 may also acquire physical/personal parameters of the user (e.g., the age, gender, and/or weight of the user) from a user input via the user input interface 130. Subsequently, the processing component 110 can determine the reaction request time according to the physical/personal parameters of the user, the user information of medicine usage (including the time of using medicine) corresponding to the assigned medicine, and the statistical information of reaction occurring time corresponding to the assigned medicine, so as to control the display component 120 to display the reaction request message at a certain time. Generally, the occurring time of reactions or whether the reactions occur varies according to individual differences. For example, the reactions may occur more quickly for lighter and younger users, and more slowly for heavier and older users. Thus, depending on the physical/personal parameters of the user, the medicine management device 100 can suitably adjust the reaction request time corresponding to different users.

Moreover, in another embodiment, in addition to determining the reaction request time according to the physical/personal parameters of the user, the user information of medicine usage corresponding to the assigned medicine, and the statistical information of reaction occurring time corresponding to the assigned medicine, the processing component 110 may also adjust the reaction request time according to user information of reaction occurring time (i.e., the actual time of reactions occurring). Specifically, the processing component 110 may adjust the reaction request time by learning. For example, the processing component 110 can control the display component 120 to display a message, so as to allow the user to input the user information of reaction occurring time (e.g., the reactions occur after 50 minutes of using the medicine). After the user information of reaction occurring time acquired via the user input interface 130, the processing component 110 can update the determined reaction request time described above by using the user information of reaction occurring time, so as to suitably adjust the reaction request time corresponding to different users.

It can be understood that, in still another embodiment, the medicine management device 100 can determine the reaction request time merely according to the user information of medicine usage corresponding to the assigned medicine and the statistical information of reaction occurring time corresponding to the assigned medicine, and the present disclosure is not limited to the embodiment described above. In a different embodiment, the reaction request time can also be determined by other information (e.g., the medicine reminding time). In still another embodiment, the processing component 110 can determine the reaction request time by using the user information of medicine usage corresponding to the assigned medicine, the user information of reaction occurring time corresponding to the assigned medicine, and at least one of the physical/personal parameters of the user.

Figure 3:
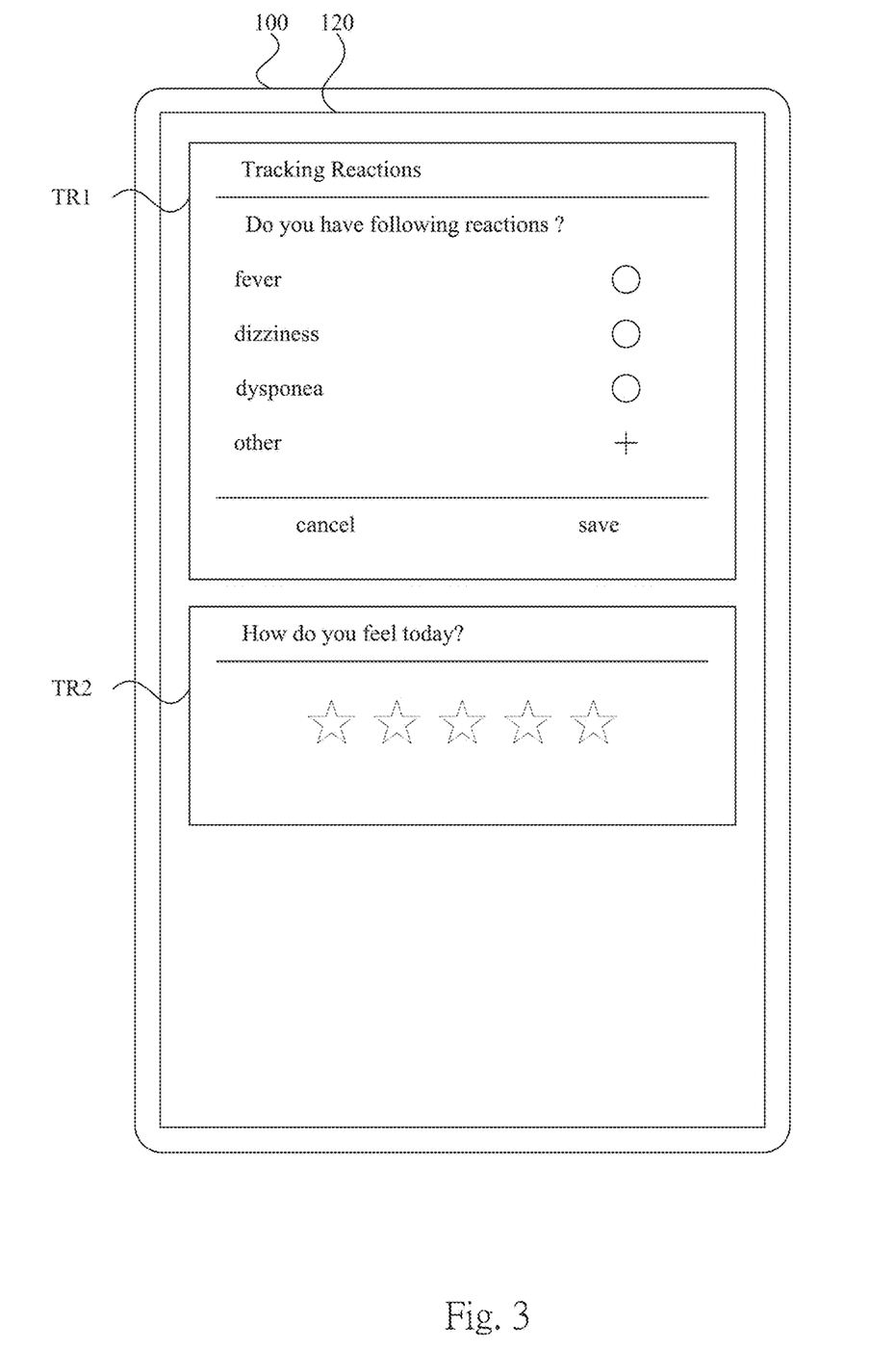
FIG. 3 illustrates an example of an operation diagram of the medicine management device in accordance with one embodiment of the present disclosure.

Reference is made to FIG. 3. For example, in an operative embodiment, the possible reactions after using medicine A may be fever and dizziness. The possible reaction after using medicine B may be dyspnoea. The using time of the medicines A, B is 12:30 PM. The reaction occurring times of medicines A, B are 1 hour. The processing component 110 can control the display component 120 to display the reaction request message TR1 at 1:30 PM according to the physical/personal parameters of the user and the using time of the medicines A, B, to ask whether the user has a fever, dizziness, and/or dyspnoea. In addition, the processing component 110 can display a request message TR2 concurrently to ask the subjective feeling of the user. The user can reply to the request messages TR1, TR2, so as to facilitate subsequent medical treatments.

It should be noted that, in this operative example, although the reaction request times of the medicines A, B are identical, and the medicine management device 100 displays the possible reactions of the medicines A, B concurrently, the present disclosure is not limited to such an embodiment. In another embodiment, the medicine management device 100 may ask the user, at 1:30 PM, whether the possible reactions (e.g., fever and dizziness) of the medicine A (the reaction occurring time of which is 1 hour) occur, and ask the user, at 2:30 PM, whether the possible reaction (e.g., dyspnoea) of the medicine B (the reaction occurring time of which is 2 hours) occurs.

In one embodiment, the processing component 110 can acquire user information of vital signs (e.g., including user information of blood pressure, user information of blood sugar, and/or user information of blood oxygen saturation). In one embodiment, the user information of vital signs includes time information corresponding to different time points of acquiring vital signs. The processing component 110 can control the display component 120 to display a vital sign request message at, before and/or after the medicine reminding time, so as to receive a corresponding user input to acquire user information of vital signs corresponding to different times. In the present disclosure, the vital signs request message can be displayed at anytime. In another embodiment, the user can input the user information of vital signs corresponding to different time via the user input interface 130 at anytime, and the present disclosure is not limited to the embodiment disclosed above.

In one embodiment, the processing component 110 can control the display component 120 to display the user information of medicine usage corresponding to the assigned medicine corresponding to different time points and the user information of vital signs corresponding to different time points concurrently. In such a manner, a doctor can concurrently view the user information of medicine usage and the user information of vital signs corresponding to different times.

In one embodiment, the processing component 110 can acquire the user information of medicine using reactions corresponding to different times by the operations described above. Subsequently, the processing component 110 can control the display component 120 to display the user information of medicine usage corresponding to the assigned medicine corresponding to different time points and the user information of medicine using reactions corresponding to different time points concurrently. In addition, the user information of vital signs corresponding to different time points can also be displayed concurrently.

Figure 4:
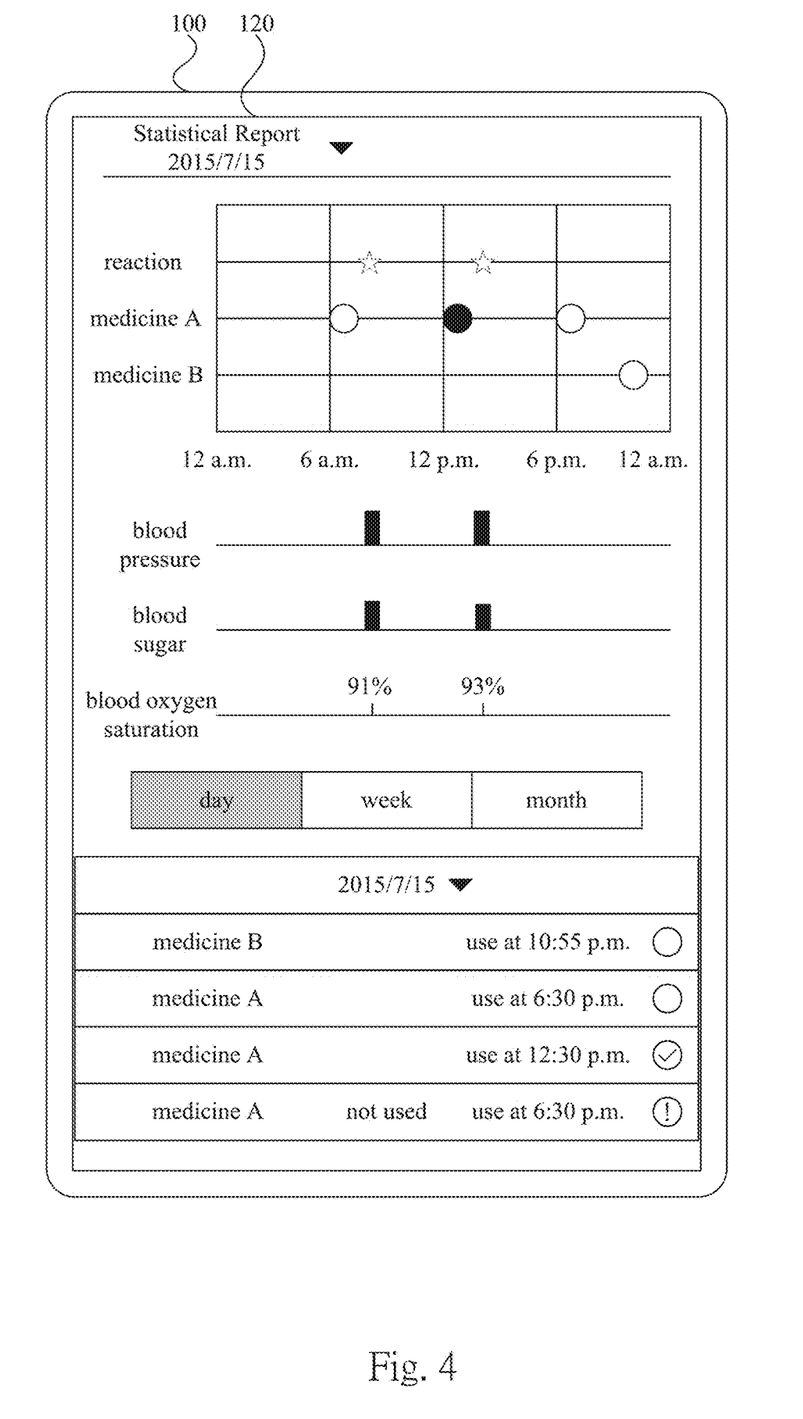
FIG. 4 illustrates an example of an operation diagram of the medicine management device in accordance with one embodiment of the present disclosure.

Reference is made to FIG. 4. For example, in one operative embodiment, the medicine management device 100 displays a statistical report of 2015 Jul. 15. In this operative embodiment, the medicine management device 100 displays the user information of medicine usage, the user information of vital signs, and the user information of medicine using reactions corresponding to different time points of the day (i.e., 2015 Jul. 15).

For example, the medicine management device 100 can display a white circle corresponding to a place corresponding to the medicine A and 6:30 AM, to indicate that the medicine A corresponding to 6:30 AM has not been used. The medicine management device 100 can display a mark indicating that reactions occur (e.g., a star mark, but not limited in this regard), a bar corresponding to the user information of blood pressure, a bar corresponding to the user information of blood sugar, user information of blood oxygen saturation corresponding to places corresponding to and 7:30 AM, so as to present the vital signs of the user corresponding to 7:30 AM and to indicate whether the side effects occur. The user can tap the star mark to watch the reactions that occurred, and that is, the user information of medicine using reactions (e.g., fever, dizziness, dyspnoea). The medicine management device 100 can display a black circle corresponding to a place corresponding to the medicine A and 12:30 PM, to indicate that the medicine A corresponding to 6:30 AM has been used. The medicine management device 100 can display a mark indicating reactions occur (e.g., a star mark), a bar corresponding to the user information of blood pressure, a bar corresponding to the user information of blood sugar, user information of blood oxygen saturation corresponding to places corresponding to and 1:30 PM, so as to present the medicine using reactions and the vital signs of the user corresponding to 1:30 PM. In addition, the medicine management device 100 can display a white circle corresponding to a place corresponding to the medicine A and 6:30 PM, and display a white circle corresponding to a place corresponding to the medicine B and 10:55 PM, to indicate that the medicine A corresponding to 6:30 PM and the medicine B corresponding to 10:55 PM are not used or have not been used yet. It should be noted that, in different embodiments, the medicine management device 100 can display the user information of medicine usage, the user information of vital signs, and the user information of medicine using reactions in another form, and the present disclosure is not limited by the embodiment described above.

In this embodiment, the medicine management device 100 can further display the medicines that should be used at 2015 Jul. 15, to allow the user or the doctor to check this information conveniently.

Figure 5:
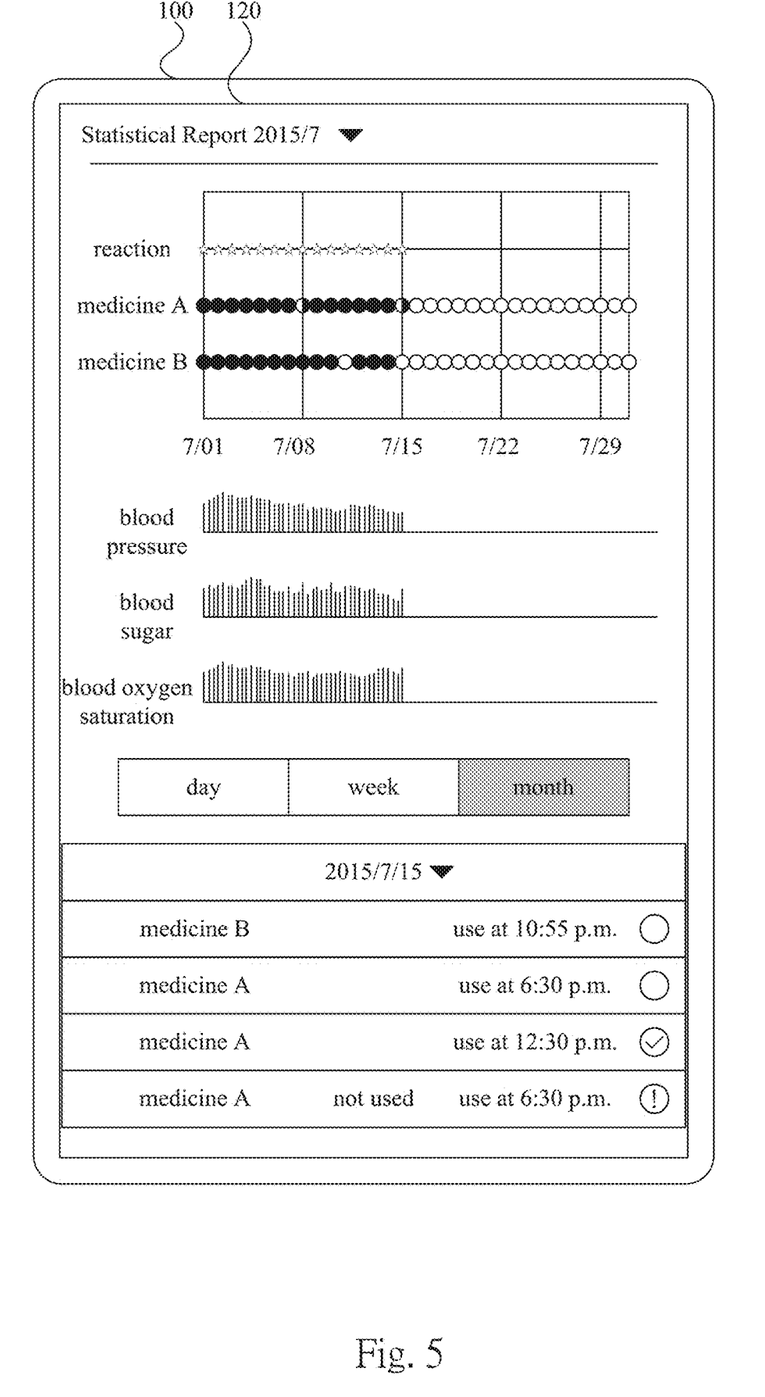
FIG. 5 illustrates an example of an operation diagram of the medicine management device in accordance with one embodiment of the present disclosure.

Reference is made to FIG. 5. In another operative example, the medicine management device 100 can display a statistical report of a month. For example, the medicine management device 100 can display a statistical report of August, 2015. In this operative embodiment, the medicine management device 100 displays the user information of medicine usage, the user information of vital signs, and the user information of medicine using reactions corresponding to different dates. The medicine management device 100 can display black circles corresponding to the places corresponding to different dates and different medicines, to indicate that the medicines corresponding to those dates that have been used completely. The medicine management device 100 can display white circles corresponding to the places corresponding to different dates and different medicines, to indicate that the medicines corresponding to those dates that completely have not been used. The medicine management device 100 can display circles that are half black and half white corresponding the places corresponding to different dates and different medicines, to indicate that portions of the medicines corresponding to those dates that have not been used.

In addition, the medicine management device 100 can display reaction marks (e.g., star marks) corresponding to different dates to indicate the medicine using reactions corresponding to the dates. In addition, the medicine management device 100 can display a bar chart corresponding to the user information of blood pressure, a bar chart corresponding to the user information of blood sugar, a bar chart corresponding to blood oxygen saturation corresponding to different times and different dates, so as to present the vital signs of the user corresponding to time and different dates.

It should be noted that, in different embodiments, the medicine management device 100 can display the user information of medicine usage, the user information of vital signs, and the user information of medicine using reactions in another form, and the present disclosure is not limited by the embodiment described above.

Details of the present disclosure are described in the paragraphs below with reference to a medicine management method in FIG. 6. However, the present disclosure is not limited to the embodiment below.

It should be noted that the medicine management method can be applied to a medicine management device having a structure that is the same as or similar to the structure of the medicine management device 100 shown in FIG. 1. To simplify the description below, in the following paragraphs, the embodiment shown in FIG. 1 will be used as an example to describe the medicine management method according to an embodiment of the present disclosure. However, the present disclosure is not limited to application to the embodiment shown in FIG. 1.

It should be noted that, in some embodiments, the medicine management method may be implemented as a computer program. When the computer program is executed by a computer, an electronic device, or the processing component 110 in FIG. 1, this executing device performs the medicine management method. The computer program can be stored in a non-transitory computer readable medium such as a ROM (read-only memory), a flash memory, a floppy disk, a hard disk, an optical disc, a flash disk, a flash drive, a tape, a database accessible from a network, or any storage medium with the same functionality that can be contemplated by persons of ordinary skill in the art to which this invention pertains.

In addition, it should be noted that in the operations of the following medicine management method, no particular sequence is required unless otherwise specified. Moreover, the following operations also may be performed concurrently or the execution times thereof may at least partially overlap.

Furthermore, the operations of the following medicine management method may be added to, replaced, and/or eliminated as appropriate, in accordance with various embodiments of the present disclosure.

Figure 6:
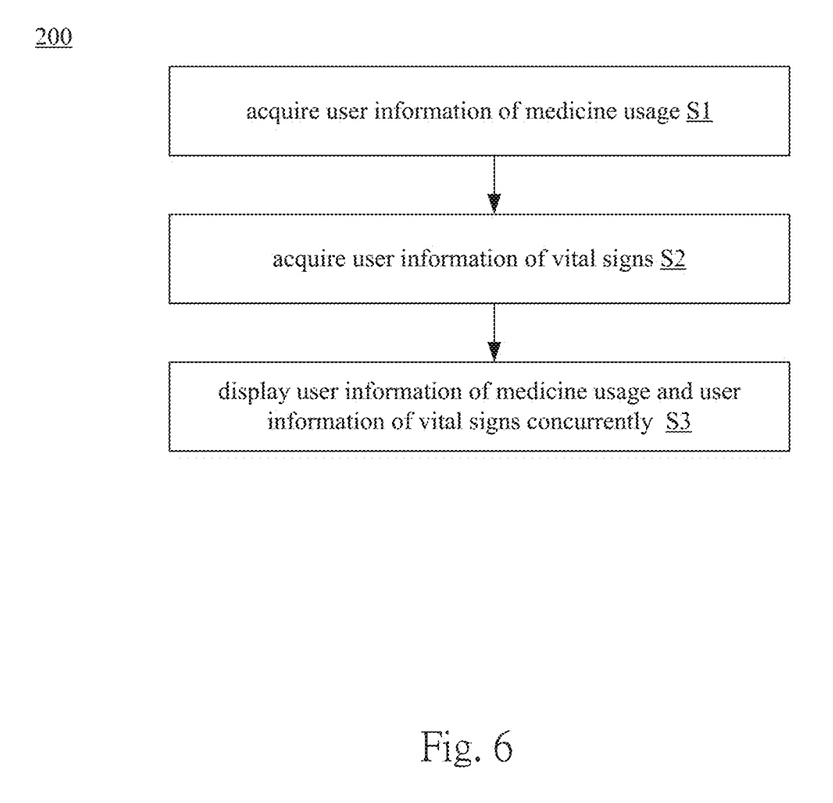
FIG. 6 is a flowchart of a medicine management method in accordance with one embodiment of the present disclosure.

Reference is made to FIG. 6. The medicine management method 200 includes the operations below.

In operation S1, the medicine management device 100 acquires user information of medicine usage corresponding to at least one assigned medicine. In one embodiment, the user information of medicine usage includes information of whether the user uses the medicine, information of the time of using the medicine, and/or information of the dose of the user. In one embodiment, the user information of medicine usage includes first time information corresponding to different time points of using the at least one assigned medicine.

In operation S2, the medicine management device 100 acquires user information of vital signs. In one embodiment, the user information of vital signs includes user information of blood pressure, user information of blood sugar, and/or user information of blood oxygen saturation. In one embodiment, the user information of medicine using reactions comprises second time information corresponding to different time points of occurring medicine using reactions.

In operation S3, the medicine management device 100 displays the user information of medicine usage with the first time information and the user information of medicine using reactions with the second time information concurrently.

It should be noted that, details of the operation described above can be ascertained with reference to the embodiments described above, and a description in this regard will not be repeated herein.

Through the operations described above, a doctor can concurrently view the user information of medicine usage and the user information of medicine using reactions corresponding to different times.

Although the present invention has been described in considerable detail with reference to certain embodiments thereof, other embodiments are possible. Therefore, the scope of the appended claims should not be limited to the description of the embodiments contained herein.

What is claimed is:

1. A medicine management method adapted to an electronic device with a camera, a processor, a display, and a touch input interface, the medicine management method comprising:

scanning a two-dimensional code via the camera;

determining whether data stored in the two-dimensional code conforms a predefined data format by the processor;

obtaining prescription information relevant to at least one assigned medicine from the two-dimensional code in response to the determination that the data stored in the two-dimensional code conforms the predefined data format;

controlling the display to display an error message in response to the determination that the data stored in the two-dimensional code does not conform the predefined data format, and then prompting manually inputting the prescription information relevant to the at least one assigned medicine;

acquiring first user information of medicine usage corresponding to the at least one assigned medicine by the processor, wherein the first user information of medicine usage comprises first time information corresponding to at least one first time point of using the at least one assigned medicine;

acquiring second user information of medicine usage corresponding to the at least one assigned medicine by the processor, wherein the second user information of medicine usage comprises second time information corresponding to at least one second time point of not using the at least one assigned medicine;

acquiring user information of medicine using reactions by the processor, wherein the user information of medicine using reactions comprises third time information corresponding to at least one third time point of one or more reactions occurring after the at least one assigned medicine is used;

displaying, by the display of the electronic device, the first user information of medicine usage with the first time information, the second user information of medicine usage with the second time information and the user information of medicine using reactions with the third time information concurrently, the displaying step comprising:

showing at least one first mark for the first user information of medicine usage corresponding to the at least one first time point on a time sequence chart;

showing at least one second mark for the second user information of medicine usage corresponding to the at least one second time point on the time sequence chart; and showing at least one third mark for the user information of medicine using reactions indicating the one or more reactions occur at at least one third time point on the time sequence chart; and displaying, by the display of the electronic device, names of the one or more reactions in response to a tap operation on a location of the touch input interface corresponding to the at least one third mark.

2. The medicine management method as claimed in claim 1 further comprising:

acquiring user information of vital signs, wherein the user information of vital signs comprises fourth time information corresponding to at least one fourth time point of acquiring vital signs;

wherein the step of displaying the first user information of medicine usage with the first time information, the second user information of medicine usage with the second time information and the user information of medicine using reactions with the third time information concurrently further comprises:

displaying the first user information of medicine usage with the first time information, the second user information of medicine usage with the second time information, the user information of medicine using reactions with the third time information and the user information of vital signs with the fourth time information concurrently.

3. The medicine management method as claimed in claim 2, wherein the user information of vital signs further comprises user information of blood pressure, user information of blood sugar, user information of blood oxygen saturation, or a combination thereof.

4. The medicine management method as claimed in claim 1, wherein the step of acquiring the user information of medicine using reactions comprises:

determining a reaction request time for displaying a reaction request message according to the first to third time information, and a user age and a user weight in at least one personal parameter;

adjusting the reaction request time earlier corresponding to that the user age is relatively young and the user weight is relatively light;

adjusting the reaction request time later corresponding to that the user age is relatively old and the user weight is relatively heavy;

displaying, by the display of the electronic device, the reaction request message at the reaction request time; and acquiring the user information of medicine using reactions from a user reply operation corresponding to the reaction request message.

5. The medicine management method as claimed in claim 4, wherein the step of determining the reaction request time comprises:

acquiring statistical information of reaction occurring time corresponding to the at least one assigned medicine; and determining the reaction request time according to the first to third time information, the user age and the user weight in the at least one personal parameter, and the statistical information of reaction occurring time corresponding to the at least one assigned medicine.

6. The medicine management method as claimed in claim 1 further comprising:

acquiring a daily schedule, the daily schedule comprising a waking time, a sleeping time and meal times;

acquiring a medicine instruction of the at least one assigned medicine;

determining at least one medicine reminding time according to the medicine instruction of the at least one assigned medicine and the daily schedule; and executing a medicine reminding operation according to the medicine reminding time.

7. The medicine management method as claimed in claim 1 further comprising:

acquiring a medicine instruction of the at least one assigned medicine and a prescribed quantity of the at least one assigned medicine;

calculating a time for going back to a doctor according to the medicine instruction of the at least one assigned medicine and the prescribed quantity of the at least one assigned medicine; and executing a reminding operation for going back to a doctor according to the calculated time for going back to a doctor.

8. The medicine management method as claimed in claim 7 further comprising:

acquiring hospital department information of prescription corresponding to the at least one assigned medicine, medicine information corresponding to the at least one assigned medicine, and doctor information of prescription corresponding to the at least one assigned medicine according to the two-dimensional code; and adjusting the time for going back to a doctor according to at least one of the hospital department information of prescription corresponding to the at least one assigned medicine, medicine information corresponding to the at least one assigned medicine, and doctor information of prescription corresponding to the at least one assigned medicine.

9. A medicine management device comprising:
a display;

a touch input interface;
a camera configured to scan a two-dimensional code; and
a processor electrically connected to the display, wherein the processor is configured for:
  determining whether data stored in the two-dimensional code conforms a predefined data format;
  obtaining prescription information relevant to at least one assigned medicine from the two-dimensional code in response to the determination that the data stored in the two-dimensional code conforms the predefined data format;
  acquiring first user information of medicine usage corresponding to the at least one assigned medicine, wherein the first user information of medicine usage comprises first time information corresponding to at least one first time point of using the at least one assigned medicine;
  acquiring second user information of medicine usage corresponding to the at least one assigned medicine, wherein the second user information of medicine usage comprises second time information corresponding to at least one second time point of not using the at least one assigned medicine;
  controlling the display to display an error message in response to the determination that the data stored in the two-dimensional code does not conform the predefined data format, and then prompting manually inputting the prescription information relevant to the at least one assigned medicine;
  acquiring user information of medicine using reactions, wherein the user information of medicine using reactions comprises third time information corresponding to at least one third time point of one or more reactions occurring after the at least one assigned medicine is used;
  controlling the display to display a time sequence chart, to show at least one first mark for the first user information of medicine usage indicating the at least one assigned medicine is used at the at least one first time point on the time sequence chart, and to show at least one second mark for the second user information of medicine usage indicating the at least one assigned medicine is not used at the at least one second time point on the time sequence chart, and to show at least one third mark for the user information of medicine using reactions indicating the one or more reactions occur at at least one third time point on the time sequence chart; and
  controlling the display to display names of the one or more reactions in response to a tap operation on a location of the touch input interface corresponding to the at least one third mark.

10. The medicine management device as claimed in claim 9, wherein the processor is further configured for:
  acquiring user information of vital signs, wherein the user information of vital signs comprises fourth time information corresponding to at least one fourth time point of acquiring vital signs; and
  controlling the display to display the first user information of medicine usage with the first time information, the second user information of medicine usage with the second time information, the user information of medicine using reactions with the third time information and the user information of vital signs with the fourth time information concurrently.

11. The medicine management device as claimed in claim 10, wherein the user information of vital signs further comprises user information of blood pressure, user information of blood sugar, user information of blood oxygen saturation, or a combination thereof.

12. The medicine management device as claimed in claim 9, wherein the processor is further configured for:
  determining a reaction request time for displaying a reaction request message according to the first to third time information and at least one personal parameter;
  adjusting the reaction request time earlier corresponding to that the user age is relatively young and the user weight is relatively light;
  adjusting the reaction request time later corresponding to that the user age is relatively old and the user weight is relatively heavy;
  controlling the display to display the reaction request message for acquiring a user input at the reaction request time; and
  acquiring the user information of medicine using reactions from a user reply operation corresponding to the reaction request message.

13. The medicine management device as claimed in claim 12, wherein the processor is further configured for:
  acquiring statistical information of reaction occurring time corresponding to the at least one assigned medicine; and
  determining the reaction request time according to the first to third time information, the user age and the user weight in the at least one personal parameter, and the statistical information of reaction occurring time corresponding to the at least one assigned medicine.

14. The medicine management device as claimed in claim 9, wherein the processor is further configured for:
  acquiring a daily schedule, the daily schedule comprising a waking time, a sleeping time and meal times;
  acquiring a medicine instruction of the at least one assigned medicine;
  determining at least one medicine reminding time according to the medicine instruction of the at least one assigned medicine and the daily schedule; and
  executing a medicine reminding operation according to the medicine reminding time.

15. The medicine management device as claimed in claim 9, wherein the processor is further configured for:
  acquiring a medicine instruction of the at least one assigned medicine and a prescribed quantity of the at least one assigned medicine according to the two-dimensional code;
  calculating a time for going back to a doctor according to the medicine instruction of the at least one assigned medicine and the prescribed quantity of the at least one assigned medicine; and
  executing a reminding operation for going back to a doctor according to the calculated time for going back to a doctor.

16. The medicine management device as claimed in claim 15, wherein the processor is further configured for:
  acquiring hospital department information of prescription corresponding to the at least one assigned medicine, medicine information corresponding to the at least one assigned medicine, and doctor information of prescription corresponding to the at least one assigned medicine; and
  adjusting the time for going back to a doctor according to at least one of the hospital department information of prescription corresponding to the at least one assigned medicine, medicine information corresponding to the at least one assigned medicine, and doctor information of prescription corresponding to the at least one assigned medicine.

17. A medicine management method adapted to an electronic device with a camera, a processor, a display, and a touch input interface, the medicine management method comprising:

scanning a two-dimensional code via the camera;

determining whether data stored in the two-dimensional code conforms a predefined data format by the processor;

obtaining prescription information relevant to at least one assigned medicine from the two-dimensional code in response to the determination that the data stored in the two-dimensional code conforms the predefined data format;

controlling the display to display an error message in response to the determination that the data stored in the two-dimensional code does not conform the predefined data format, and then prompting manually inputting the prescription information relevant to the at least one assigned medicine;

acquiring first to third user information of medicine usage corresponding to the at least one assigned medicine by the processor, wherein the first user information of medicine usage comprises first time information corresponding to at least one first time point of using the at least one assigned medicine, wherein the second user information of medicine usage comprises second time information corresponding to at least one second time point of not using the at least one assigned medicine, and wherein the third user information of medicine usage comprises third time information corresponding to at least one third time point of partially using the at least one assigned medicine;

acquiring user information of medicine using reactions, wherein the user information of medicine using reactions comprises fourth time information corresponding to at least one fourth time point of one or more reactions occurring after the at least one assigned medicine is used; and displaying, by the display of the electronic device, the first to third user information of medicine usage first to third with the first to third time information and the user information of medicine using reactions with the fourth time information concurrently, the displaying step comprising:

showing at least one first mark for the first user information of medicine usage corresponding to the at least one first time point on a time sequence chart;

showing at least one second mark for the second user information of medicine usage corresponding to the at least one second time point on the time sequence chart;

showing at least one third mark for the third user information of medicine usage corresponding to the at least one third time point on the time sequence chart; and showing at least one fourth mark for the user information of medicine using reactions indicating the one or more reactions occur at at least one fourth time point on the time sequence chart.

18. The medicine management method as claimed in claim 17 further comprising:

acquiring information of possible reactions of the at least one assigned medicine, wherein the reaction request message corresponds to the information of possible reactions of the at least one assigned medicine.

19. The medicine management method as claimed in claim 1, wherein the step of acquiring user information of medicine using reactions comprises:

determining a reaction request time for displaying a reaction request message according to the first time point of the user taking the at least one assigned medicine and statistical information of reaction occurring time corresponding to the at least one assigned medicine, wherein the reaction request time corresponds to an estimated actual time of one or more reactions occurring subsequent to the user taking the at least one assigned medicine;

displaying, by the display of the electronic device, the reaction request message at the reaction request time; and receiving, via the touch input interface, user input of the user information of medicine using reactions.

20. The medicine management method as claimed in claim 19, wherein determining the reaction request time is performed further according to at least one personal parameter of the user.

* * * * *